United States Patent [19]
Sparago

[11] Patent Number: 6,047,241
[45] Date of Patent: Apr. 4, 2000

[54] METHOD OF SELECTIVE CORROSION RATE ANALYSIS FOR A FLUID PROCESSING PLANT

[76] Inventor: Michael T. Sparago, 5 Blueberry Hill Rd., Wilbraham, Mass. 01095

[21] Appl. No.: 08/956,909

[22] Filed: Oct. 23, 1997

[51] Int. Cl.[7] .............................. G01N 27/00; G21C 17/00
[52] U.S. Cl. .............................. 702/34; 702/36; 702/179; 376/305; 73/804
[58] Field of Search .................................. 702/33, 34, 35, 702/36, 179, 180; 73/86, 592, 804; 376/249, 305

[56] References Cited

U.S. PATENT DOCUMENTS

| | | | |
|---|---|---|---|
| 4,298,955 | 11/1981 | Munday et al. | 364/900 |
| 4,440,862 | 4/1984 | Cheng et al. | 436/6 |
| 4,539,846 | 9/1985 | Grossman | 73/579 |
| 4,712,182 | 12/1987 | Wakamori et al. | 702/36 |
| 4,751,461 | 6/1988 | McWhirter et al. | 324/221 |
| 4,796,466 | 1/1989 | Farmer | 702/51 |
| 4,909,091 | 3/1990 | Elmann et al. | 73/866.5 |
| 4,935,195 | 6/1990 | Palusamy et al. | 73/592 |
| 4,998,208 | 3/1991 | Buhrow et al. | 702/34 |
| 5,311,562 | 5/1994 | Palusamy et al. | 376/215 |

*Primary Examiner*—Marc S. Hoff
*Assistant Examiner*—Bryan Bui
*Attorney, Agent, or Firm*—Malcolm J. Chisholm, Jr.

[57] ABSTRACT

A method of selective corrosion rate analysis is shown for generating an inspection and replacement schedule for a fluid processing plant. The method includes the steps of identifying a system from a division of the plant into one or more systems wherein each system has mechanical components that are expected to experience a common corrosion environment, and wherein each system has at least one thickness measurement location for performing thickness inspections. The next steps are establishing system corrosion data for each thickness measurement location and running the data through a plurality of corrosion engineering models. Running the corrosion engineering models includes coordinating the system corrosion data of the thickness measurement locations into a plurality of physical relationship data groups, and applying a plurality of statistical distribution/goodness-of-fit tests to each physical relationship data group. The final step is selecting a best fitting corrosion engineering model for generating an inspection schedule for the fluid containment components within each system of the plant. In a preferred embodiment of the method of selective corrosion rate analysis, the step of running the corrosion engineering models includes the additional step of identifying sub-populations within the application of the statistical distribution/goodness-of-fit tests so that identification of such sub-populations assists the user in identifying unknown corrosion mechanisms, and establishing specific inspection schedules for the sub-populations.

20 Claims, 3 Drawing Sheets

FIG. 1

FIG.3

METHOD OF SELECTIVE CORROSION RATE ANALYSIS FOR A FLUID PROCESSING PLANT

BACKGROUND OF THE INVENTION

The present invention relates to methods for monitoring corrosion rates of mechanical components of fluid processing plants. As is well known in the art, a complex fluid processing plant such as an oil refinery or a chemical processing plant includes many different types of mechanical fluid containment components, such as piping, valves, pressure vessels, heat exchangers, fired heaters, atmospheric tankage, etc. Each such component will corrode at a specific rate that is a function of many variables including for example types of fluid within the component, fluid flow conditions, materials of construction, operating temperatures and pressures of fluids within the component, along with many other often complex factors.

Safe and efficient operation of such fluid processing plants requires that each mechanical component be inspected at regular intervals to monitor a rate of corrosion within the component so that the component may be replaced or taken out of service to avoid a corrosion-triggered breach of the component and a resulting failure of the plant, with potentially catastrophic results. Schedules generated for inspection and/or replacement of such mechanical components are generated based on optimizing safe and reliable plant operation while minimizing inspection and replacement costs. An important factor in generating such inspection schedules is a necessity of inspection personnel focusing attention on critical components having a high probability of compromising plant safety and reliability in the event of a corrosion caused breach of such a critical component. For example, scheduling inspection of all components more frequently than required to insure safe and reliable plant operation may actually divert inspection resources from the critical components, thereby over using inspection resources inefficiently while actually jeopardizing safe and reliable plant operation.

Many methods have been developed to generate efficient corrosion rate inspection schedules for fluid processing plants. Recent methods may include modern, computer-based organization and manipulation of large amounts of data related to specific inspection locations associated with all or exemplary components within the plant. Typical of such modern methods is the "Piping Corrosion Monitoring System Calculating Risk-Level Safety Factor Producing An Inspection Schedule" disclosed in U.S. Pat. No. 4,998,208 issued on Mar. 5, 1991 to Buhrow, et al. and assigned to the Standard Oil Company of Cleveland Ohio, which patent is hereby incorporated herein by reference.

The corrosion monitoring system of Buhrow et al. discloses a method including a first step of dividing a fluid containment plant into circuits wherein each circuit includes components made of similar materials exposed to common corrosive agents operating under similar operating conditions. In the next step individual inspection locations or points are defined within each circuit and historical corrosion rate data is assembled that includes actual thickness measurements at each inspection point, wherein the measurements are associated with specific times of measurement of the inspection point. Next, a highest rate of corrosion for each inspection point is determined based typically on analysis of a plurality of "test cases" which are established for each circuit. Some of the test cases are based on corrosion mechanisms that tend to corrode an entire section of pipe (e.g., to split a pipe), while other test cases are based on corrosion mechanisms tending to corrode specified points within a pipe or vessel (e.g., by pitting the component). The test case yielding the highest rate of corrosion for a specific inspection point is selected. Next a risk-level safety factor is established for each circuit and is calculated from a plurality of factors including operating pressures and temperatures of the circuit; relative degree of hazard to humans of the fluids in the circuit; potential of those materials to spontaneously ignite in the atmosphere; and the location of the circuit relative to valued property that could be damaged in light of a breach within the circuit. Finally, the risk-level safety factor is combined with the test-case generated rate of corrosion to produce an inspection date for each inspection point, and then an inspection schedule for the circuit and the plant is generated from the inspection dates.

As is apparent, the Buhrow et al. corrosion monitoring system is heavily dependent upon identification of a specific circuit. An exemplary circuit shown and described in that patent is identified as "a light gas-oil processing line" that includes many piping sections, valves, drains, reducers, vents, fittings interconnecting the components, etc. The circuit-based test cases that define a plurality of potential corrosion rates combined with the circuit-based risk-level safety factors essentially form a basis for the next inspection date for a particular inspection point. Additionally, after definition of the test cases, the Buhrow et al. method does not provide for any mechanism to re-define the circuits. Therefore, generation of shorter interval, higher frequency inspection schedules for the entire circuit is the primary result of inspections revealing higher corrosion rates. While such a method may be cautiously conservative, because the method is based on definition and test case analysis of static circuits it is inherently incapable of identifying many corrosion mechanisms and trends that may develop, particularly when such corrosion mechanisms and trends are localized within the circuit. In circuits where such localized conditions are present, that method may wastefully over-inspect some inspection points while dangerously under-inspecting other points.

In particular, the Buhrow et al. method establishes historical corrosion rate data based on an analysis of an assumed common corrosive environment even when the data reveals that such an environment does not exist in the circuit as defined. When analyzing corrosion rate data, it is of vital importance to recognize that process conditions, hence the corrosion behavior in a fluid processing system, may not observe the intended engineering/design criteria and ideal or expected fluid processing conditions. It is frequently observed that unanticipated conditions occur involving possibly flow rate changes, phase changes, particulate and/or fluid contaminants that change actual corrosion rate mechanisms within a so-called circuit. For example, an entrained particulate which forms in or is transported by a process fluid may dramatically erode internal surfaces of a change of direction fitting such as an elbow or tee fitting while having no discernable effect on the underlying fluid-generated corrosion rate on linear piping or storage containers. The Buhrow et al. method would rely on the conservative circuit-based test case averages and risk-level safety factor to have an adequately frequent inspection schedule to lead to replacement of the change of direction and other components in the circuit prior to breach, and would be unable to identify this primary corrosion mechanism at work in the circuit.

Additionally, the circuit-based test case calculations of corrosion rates in Buhrow et al. assume the corrosion rate data follows but one statistical distribution, namely a Gaussian or normal distribution. For example, the "circuit formula adjusted average rate" inflates the circuit average rate by a multiple of circuit corrosion rate standard deviations, with adjustments for the number of inspection points in the circuit, and thereby attempts to estimate a maximum circuit rate based on measurements of corrosion rates at individual inspection points. The calculation used therein is valid only when the corrosion rate data follows a normal distribution. However, recent work on fluid processing plants by the inventor of the "Method of Selective Corrosion Rate Analysis" invention described hereinbelow including over 240,000 inspection points in over 2,200 circuits has revealed that less than ten per cent (10%) of the circuits include corrosion rate data exhibiting a normal distribution. In circuits having sub-populations of corrosion rate data and those which may additionally exhibit non-normal corrosion rate behavior, using an inflated circuit average corrosion rate based on a normal distribution may result in over-inspection of points which follow a low corrosion rate distribution and under-inspection of sub-populations of points in a high corrosion rate distribution, so that none of the points in the system are optimally inspected.

The Buhrow et al. method therefore must select the highest test-case average corrosion rate, and then modify that rate by the risk-level safety factor to produce an inspection schedule because the static, rigid test-case comparative models cannot accurately describe all active corrosion mechanisms at work in the circuit. Neither Buhrow et al. nor any known methods of corrosion rate analysis of a fluid processing plant provides a model suitable for application of inspection data from which a corrosion inspection schedule may be generated for the plant that effectively quantifies and optimizes both inspection cost and probability of failure.

Accordingly, it is the general object of the present invention to provide a method of selective corrosion rate analysis for a fluid processing plant that overcomes problems of the prior art.

It is a more specific object to provide a method of selective corrosion rate analysis that enables a user to define a plurality of corrosion engineering models and select corrosion engineering models appropriate for the equipment and fluid(s) processed in the plant.

It is another specific object to provide a method of selective corrosion rate analysis that enables a user to identify multiple corrosion mechanisms at work in systems throughout the plant.

It is yet another specific object to provide a method of selective corrosion rate analysis that enables a user to generate a dynamic library of data that serves as a basis for modifying existing corrosion engineering models and developing new corrosion engineering models to enhance the analysis of subsequent inspection data.

It is another object to provide a method of selective corrosion rate analysis that enables a user to generate sub-sets of data groups within the plant for separate inspection schedules based upon identification and analysis of multiple corrosion mechanisms.

These and other objects and advantages of the present invention will become more readily understood when the following description is read in conjunction with the accompanying drawings.

SUMMARY OF THE INVENTION

A method of selective corrosion rate analysis is disclosed for generating inspection and replacement schedules for a fluid processing plant. The method includes the steps of identifying a system from a division of the plant into one or more systems wherein each system has mechanical components that are expected to experience a common corrosion environment, and wherein each system has at least one thickness measurement location for performing thickness inspections. The next steps are establishing system corrosion data for each thickness measurement location and running the data through a plurality of corrosion engineering models. Running the corrosion engineering models includes coordinating corrosion rate data of the thickness measurement locations into a plurality of physical relationship data groups, and applying a plurality of statistical distribution/goodness-of-fit tests to each physical relationship data group. The final step is selecting a best fitting corrosion engineering model for generating inspection and replacement schedules for the fluid containment components within each system of the plant.

In a preferred embodiment of the method of selective corrosion rate analysis, the step of running the corrosion engineering models includes the additional step of identifying sub-populations within the application of the statistical distribution/goodness-of-fit tests so that identification of such sub-populations assists the user in identifying general and localized corrosion mechanisms, and establishing specific inspection schedules for the sub-populations. In additional embodiments of the method of selective corrosion rate analysis a corrosion engineering model library integrates ongoing corrosion engineering model results with historical corrosion rate data and other information to thereby modify the corrosion engineering models or develop new models that may be required to improve identification of all active corrosion mechanisms in specific systems and hence the entire plant. Further embodiments of the method of selective corrosion rate analysis include steps of integrating system risk and reliability criteria and inspection cost data with generation of an inspection/replacement schedule.

In use of the method of selective corrosion rate analysis, the fluid processing plant such as an oil refinery is divided into systems having or that are expected to contain common corrosion environments. For purposes of explanation, one such system could consist of two types of mechanical components being straight pipe and ninety degree elbows of two different sizes being four (4) inch and six (6) nominal pipe sizes, having fifty-five different thickness measurement locations ("TMLs"). For each system, design and construction data would be drawn from sources such as initial plant design specifications and/or fabrication records and this data would be integrated with results from past thickness inspections. Then the TMLs would be coordinated into a plurality of physical relationship data groups. For example one such group could be all system TMLs grouped according to their locations in different size components (e.g., 4 inch and 6 inch nominal pipe sizes); another group could be all system TMLs grouped according to their locations in different components (e.g., straight pipes, elbows); and an additional group could be all system TMLs grouped according to their locations at differing orientations within the components (e.g., an outside radius, and inside radius, a top of a pipe, a bottom of a pipe, etc.). A further physical relationship data group could be TMLs grouped according to their positional locations in zones of varying localized corrosion rates relative to TMLs outside such zones. Next the system corrosion data associated with the TMLs of each physical relationship data group is separately applied to a plurality of statistical distributions, such as Normal, Log Normal, Weibull, etc. A goodness-of-fit test is then applied to each statistical distribution result for each physical relationship data group in order to identify the combined physical relationship data group and statistical distribution that gives the best fit of the system corrosion data to the known, contemporary data, and therefore best describes actual corrosion behavior in the system. That combination then becomes the selected corrosion engineering model most appropriate for that system, and all inspection measurement data applicable to that specific physical relationship data group is run through that selected corrosion engineering model to generate an inspection/replacement schedule for the components of that system. The same method is applied to generate inspection/replacement schedules for all systems within the plant.

DETAILED DESCRIPTION OF THE PREFERRED EMBODIMENTS

Figure 1:
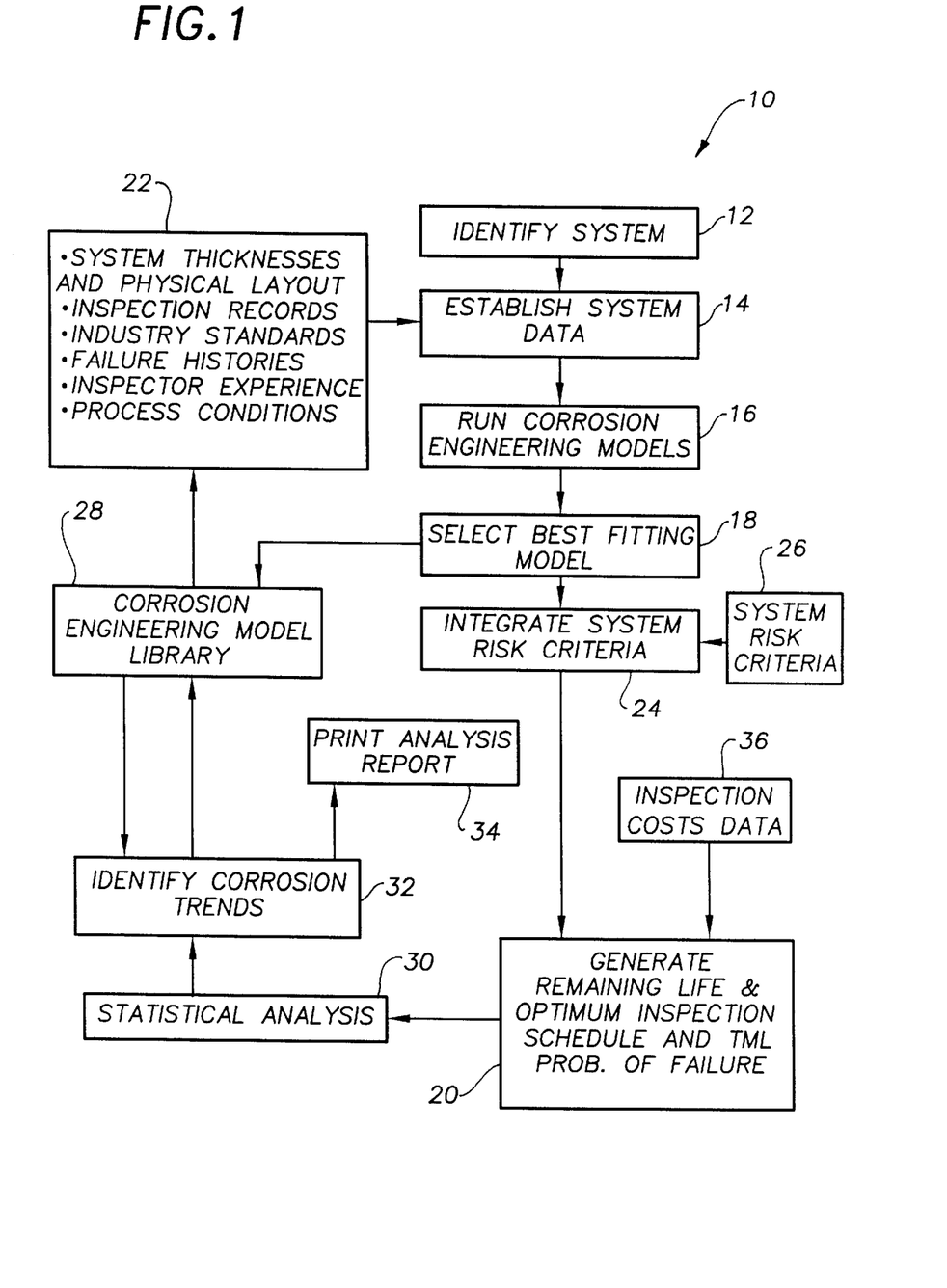
FIG. 1 is a schematic flow chart representation of the method of selective corrosion rate analysis for a fluid processing plant of the present invention showing an overview of operation of the method.

Referring to the drawings in detail, a method of selective corrosion rate analysis for generating an inspection schedule for a fluid processing plant is shown in schematic form in FIG. 1, and generally designated by the reference numeral 10. The method 10 basically includes the steps of identifying a system 12 from a division of the plant into one or more systems wherein each system has mechanical fluid containment components (not shown) that are expected to experience a common corrosive environment and each system has at least one thickness measurement location ("TML") in that system for performing thickness inspections; establishing system corrosion data 14 for each TML in the system; running the system corrosion data through a plurality of corrosion engineering models 16; and selecting a best fitting corrosion engineering model 18 for generating a remaining life and optimum inspection schedule 20 for each TML and component within the system, by running the system corrosion data through the selected best fitting corrosion engineering model, including with the schedule an estimate of a probability of that each TML will reach its retirement thickness prior to the next inspection date or another target date (e.g., a scheduled maintenance shutdown date) required by the plant's operating plan.

As shown in FIG. 1, the step of establishing system corrosion data 14 for each TML includes drawing system specific and mechanical component specific information from an historical corrosion rate data base 22 for the system that includes information from historical, design, operating and inspection records about material thicknesses of the mechanical components making up the system, drawings depicting a physical layout of the system, past inspection records of TML data in the system, industry standards regarding inspection practices and areas of vulnerability, failure histories of mechanical components operating under similar conditions to those in the system, inspector experiences regarding both the specific system and also similar systems and fluid process conditions expected within the system. The method of selective corrosion rate analysis may also include a step of integrating risk criteria 24 after the selecting a best fitting corrosion engineering model step 18 and before the generating an inspection schedule step 20, wherein the system risk criteria 26 quantitatively defines the required system reliability level, consistent with the plant's safety and operating targets. Criteria for the consequence of failure in the system (i.e., a breach of the system that permits process fluids to leave the system) may be also be incorporated into the system risk criteria 26, including other factors such as flammability of process fluids within the system, proximity of the system to humans, economic penalties of a breach of the system that permits the process fluids to leave the system, etc.

The method of selective corrosion rate analysis may also include a corrosion engineering model library 28 that receives operational information from two sources after running of the corrosion engineering models 16 on a new set of inspection data. The first source is information resulting from the selecting the best fitting model step 18 and the second source is information resulting from a statistical analysis 30 applied to all TMLs after determining the remaining life and probability of failure or retirement generating step 20, wherein the statistical analysis 30 identifies corrosion trends 32 resulting from the most recent inspection data that may differ from trends anticipated by historical data alone. This operational information is then integrated within the corrosion engineering library 28 and passed into the historical corrosion rate data base 22 to store system statistical corrosion rates and any trends identified. Corrosion rate data which did not exhibit an acceptable fit to any of the current corrosion engineering models is flagged for more in-depth analysis through modifications to existing corrosion engineering models, thereby affecting subsequent running of the corrosion engineering models 16. As will be explained in more detail below, operation of the corrosion engineering model library 22 allows for dynamic, system-data driven modifications of the method of selective corrosion rate analysis 10 in order to assist in identifying actual, active corrosion mechanisms at work in the system. The integrated operational information within the corrosion engineering model library 28 is also used in the identify corrosion trends 32 step, and the trends may be printed in an analysis report 34 along with other analysis results, as shown in FIG. 1. The method of selective corrosion rate analysis 10 may also include an integration of inspection costs data step 36 into the generation of the remaining life, optimum inspection step 20, wherein common inspection cost data is included, such as an inspector's hourly rate, number of TML's capable of inspection per hour, hours required for preparation and permitting (e.g., for access to remote TMLs such as an elevated piping system) for the TMLs in a system, special access costs such as scaffolding, number of segments to divide a system into for the purposes of inspecting and annual inflation rates for inspection costs.

The method of selective corrosion rate analysis 10 may be performed on paper with traditional mathematical and statistical operations, however because of the vast array of data associated with modern fluid processing plants, efficiencies of the system are dramatically enhanced when the selective corrosion rate analysis method 10 is operated on a modern personal computer capable of running state-of-the art statistical software for fitting data to a variety of statistical distributions and performing goodness-of-fit tests. A custom-designed, integrated statistical/database application, however, facilitates processing a large volume of data, and is generally available to those skilled in the art.

Figure 2:
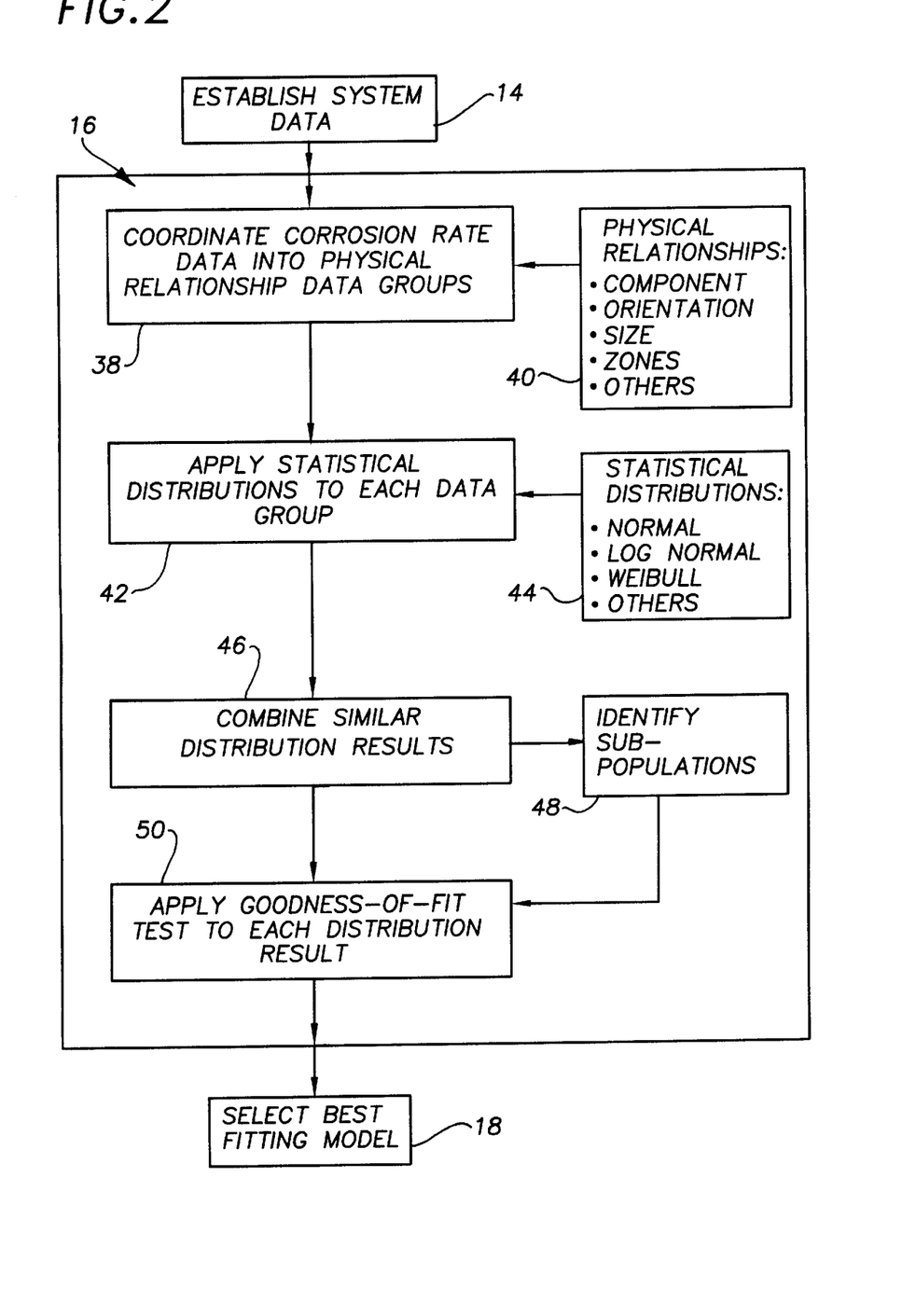
FIG. 2 is a schematic flow chart representation of a portion of the FIG. 1 flow chart showing in more detail running of corrosion engineering models of the present invention.

As seen in FIG. 2, the running of the corrosion engineering models includes the steps of first coordinating the system corrosion data for each TML into a plurality of physical relationship data groups 38. Such groups may be drawn from any potential grouping of data 40 for TMLs related to physical relationships of the TMLs in the group that may be required to identify corrosion trends found in industry standards, failure histories, inspection records or inspector experience as seen in FIG. 1 at reference numeral 22. Whenever possible, all TMLs in a system are assigned to a group to insure a thorough analysis by the corrosion engineering models. For example, the physical relationship data groups could include a first group having all of the TMLs grouped randomly. A second physical relationship data group could consist of all the system TMLs grouped according to different sized mechanical components (e.g., all 4 inch, and all 6 inch nominal pipe sizes) in which the TMLs are located. If the system additionally included ¾ inch nominal pipe size drains, TMLs in these drains would be grouped together in a separate group. A third physical relationship data group could consist of all system TMLs grouped according to different components in which the TMLs are located (e.g., straight pipes, elbows). If this system also included piping "Tees", the TMLs in these Tees would form a separate physical relationship data group.

A fourth physical relationship data group could consist of all system TMLs grouped according to their differing orientations within the components (e.g., all TMLs taken on the elbow outside radii, elbow inside radii, the top and bottom of all components, etc.). This fourth physical relationship data group is specifically designed to identify accelerated corrosion resulting from localized high and low flow conditions and/or the presence of erosive materials in the process fluid. Note that for this relationship, several orientations from an "other" grouping would be necessary (other than outer radii, inner radii, top and bottom) since the relationship data grouping seeks to identify specific corrosion mechanisms which are not generally experienced in these certain "other" orientations (TMLs taken on the East vs. West orientations, for example will generally not show the accelerated corrosion trends that this relationship seeks to identify, however, the "other" orientations serve as a basis for comparison against outer radii, inner radii, top and bottom orientations). A fifth physical relationship data group could consist of TMLs grouped according to a consecutive positional location of the TMLs forming a zone of significantly higher TML corrosion rates relative to TMLs grouped according to their positions outside the zone. The zone of higher corrosion rates could be of any length or position within the system. If the corrosion engineering model does not identify the presence of such a zone, this relationship essentially defaults to the "all TMLs" data group. This "zones" relationship is useful for locating accelerated corrosion due to the mixture of two or more process streams, high corrosion "pockets" due to the physical layout of the system, and for inadvertent changes in material of construction (e.g., piping spool piece constructed from and improper material, installed in the system).

Other potential groups of data 40 could be used depending upon the nature of the system so that the physical relationship data groups are structured to juxtapose TMLs that may be exposed to any potentially differing corrosion mechanisms than those anticipated by information derived and analyzed under traditional methods from the historical corrosion rate data base 22.

After the physical relationship data groups are coordinated 38, the next step is application of a plurality of statistical distributions to each physical relationship data group 42. The particular statistical distributions to be applied are selected from a variety of known statistical distributions 44 such as Normal, Log Normal, Weibull, etc. Next, results of the statistical distribution of each data group that are not significantly different are merged or combined 46. If the system consists of a single distribution of corrosion rates, the physical relationship data groups will merge into the "all TMLs" data group. If two or more physical relationship groups remain from a particular relationship after merging groups which are not significantly different, the remaining groups are considered to be sub-populations and will have different corrosion rate distributions.

The next step in running the corrosion engineering models is application of a goodness-of-fit test 50 to the combined physical relationship data groups and to any sub-populations. As explained in more detail below, results of the goodness-of-fit tests will identify a combination of a particular physical relationship data group with a particular statistical distribution applied to that data group which produces the most accurate fit of the system corrosion data to most recent known inspection test data, and therefore best describes actual corrosion behavior in the system. That combination is then selected as the best fitting corrosion engineering model 18 for that system, and all current inspection data is run through that selected corrosion engineering model to generate the remaining life and optimum inspection schedule for the system.

Figure 3:
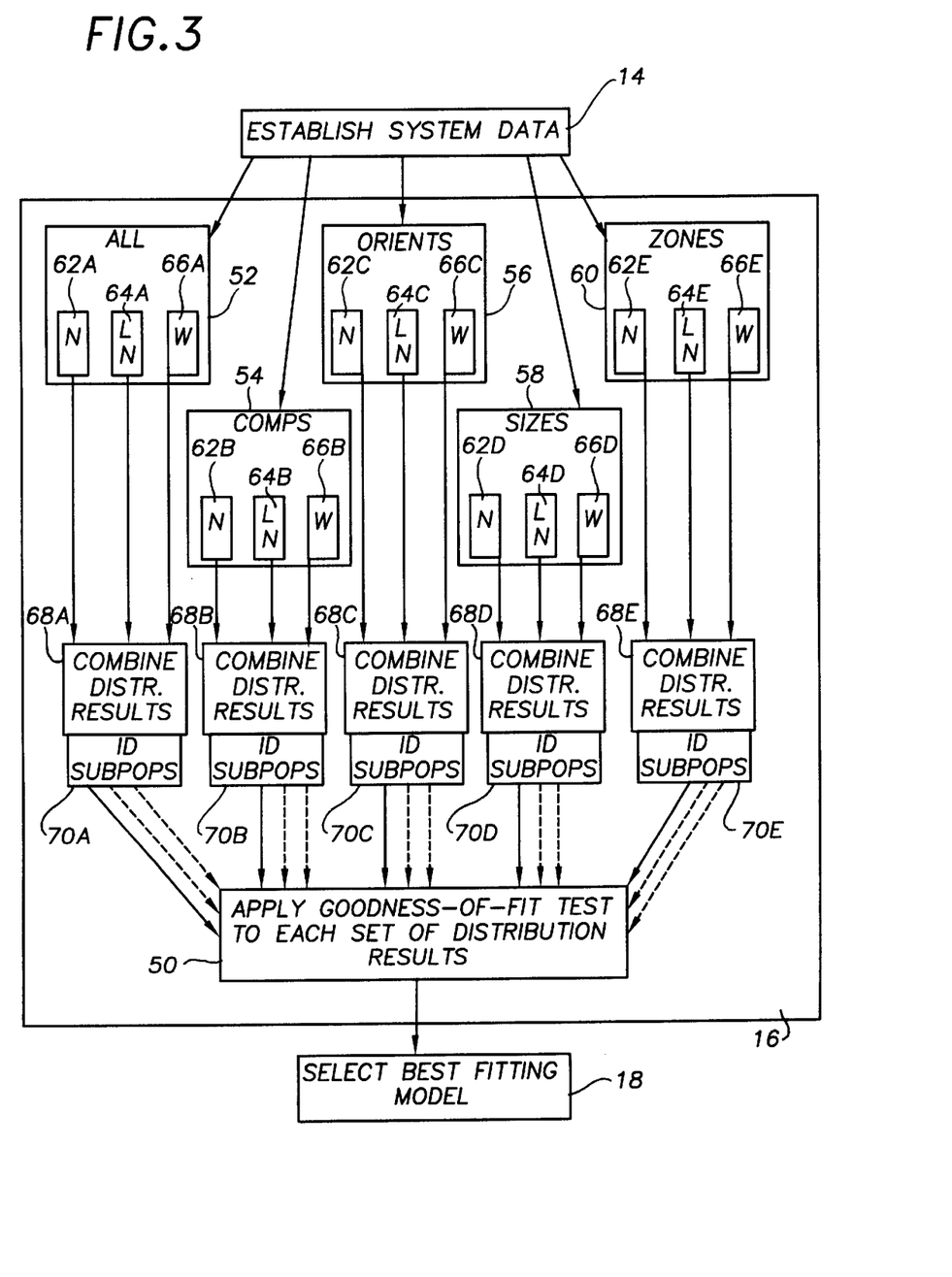
FIG. 3 is a schematic flow chart representation of an exemplary operation of the FIG. 2 corrosion engineering models.

Actual running of the corrosion engineering models is shown in more detail in the schematic presentation of FIG. 3. Following the example described above, five groups of physical relationship data groups are coordinated by drawing corrosion rate data for each TML in each of the five groups from the established system corrosion data 14. A first physical relationship data group 52 includes all of the TMLs in the system, and is labelled "ALL" at reference numeral 52 in FIG. 3. A second group 54 includes all system TMLs grouped according to their locations in different kinds of mechanical components, and is abbreviated "COMPS" at 54. A third group 56 includes all system TMLs grouped according to their locations at differing orientations within the mechanical components, and is abbreviated "ORIENTS". A fourth group 58 includes all system TMLs grouped according to their locations in different sized components, and is abbreviated "SIZES". And a fifth group 60 labelled "ZONES" includes TMLs grouped according to their positional locations in zones of varying localized corrosion rates relative to corrosion rates of TMLs outside such zones.

After coordination of the system corrosion data into the corrosion rate data for the TMLs in each of the five physical relationship data groups 52, 54, 56, 68, 60, in the FIG. 3 example, three statistical distributions are applied to the corrosion rate date of each of the five groups. Application of a Normal statistical distribution 62A, 62B, 62C, 62D, 62E to each group is shown in the boxes labelled "N", while application of a Log Normal distribution 64A, 64B, 64C, 64D, 64E is shown in the boxes labelled "LN", and application of a Weibull statistical distribution 66A, 66B, 66C, 66D, 66E is shown in the boxes labelled "W". Next, any of the results of the statistical distributions within each of the five physical relationship data groups 52, 54, 56, 58, 60 are combined if not significantly different 68A, 68B, 68C, 68D, 68E, as represented in the boxes labelled "COMBINE DISTR. RESULTS". By the phrase "if not significantly different", it is meant that the physical relationship data groups are not statistically different where the preferred method is to utilize the log likelihood ratio test (Wayne Nelson, "Accelerated Testing", John Wiley, 1990) which compares the sum of individual group log likelihoods less a merged log likelihood to the chi-square statistic.

Next any results of the statistical distributions within each of the five physical relationship data groups 52, 54, 56, 58, 60 that contain more than one distribution are considered to be and identified as sub-populations 70A, 70B, 70C, 70D, 70E, as represented in the FIG. 3 boxes labelled "ID SUBPOPS", with each remaining group having a unique corrosion distribution. Finally in running the corrosion engineering models 16, application of a goodness-of-fit test 50 is made to each set of statistical distribution results, including any combined (or merged) set of results, as well as to any identified sub-populations. (In FIG. 3, the two broken lines running between each of the "ID Subpops" boxes 70A, 70B, 70C, 70D, 70E to the "Apply Goodness-Of Fit Test" box 50 represent a possibility that there may be one set of combined distribution results (e.g., one unbroken line), or a set of combined sets of distribution results and an identified sub-population, or two sets of sub-populations, etc.) As indicated above, application of the goodness-of-fit test, (which may be one of many such tests well-know in the statistical arts, such as specific tests detailed below) will identify which combination of physical relationship data group and statistical distribution provides the best fit of the system corrosion data to most recent known inspection test data, and therefore best describes actual corrosion behavior in the system. That combination will then be selected as defining the best fitting corrosion engineering model 18 for running of all inspection measurement data produced in the system. For example, if the goodness-of-fit test indicated that the combination of the third physical relationship data group 56 ("ORIENTS", or TMLS at differing orientations) with a Weibull statistical distribution 66C produced the best fit of the historical corrosion rate-based system corrosion data to actual inspection results, then the selected corrosion engineering model would include a Weibull statistical distribution applied to TMLs grouped according to their differing orientations on mechanical components (e.g., at an outside and inside radius of an elbow, or at a top and of a straight pipe, etc.). Therefore, that particular corrosion engineering model, a Weibull distribution-orientation physical relationship 56, 66C corrosion engineering model would be used for generating remaining life and optimum inspection schedules 20 for the system.

A specific example of use of the method of selective corrosion rate analysis 10 for generating a remaining life and optimum inspection schedule for a fluid processing with explanatory tables and exemplary calculations follows. The example consists of 55 thickness measurement locations ("TMLs"), two types of components (straight pipe and ninety degree (90°) elbows), and two different pipe sizes (4 inch 6 inch nominal pipe sizes). All such mechanical components have similar materials of construction, and three sets of thickness measurements are taken at various orientations around the components. The historical corrosion rate data and long-term corrosion rates ("LTCR") are shown in Table 1 "Inspection and Corrosion Rate Data".

TABLE 1

Inspection And Corrosion Rate Data

| TML | Size & Component Type | Orientation of TML on Component | Minimum Required Thickness | Initial Insp Date | Initial Insp Thickness | Previous Insp Date | Previous Insp Thickness | Last Insp Date | Last Insp Thickness | LTCR mils/yr |
|---|---|---|---|---|---|---|---|---|---|---|
| 1.01 | 6" PIPE | North | 0.62 | 8/1/93 | 1.440 | 2/1/95 | 1.440 | 5/1/96 | 1.438 | 0.7 |
| 1.02 | 6" PIPE | South | 0.62 | 8/1/93 | 1.422 | 2/1/95 | 1.420 | 5/1/06 | 1.415 | 2.5 |
| 1.03 | 6" PIPE | East | 0.62 | 8/1/93 | 1.434 | 2/1/95 | 1.433 | 5/1/96 | 1.432 | 0.7 |
| 1.04 | 6" PIPE | West | 0.62 | 8/1/93 | 1.434 | 2/1/95 | 1.433 | 5/1/96 | 1.428 | 2.2 |
| 3.01 | 6" ELL | Outer Radius | 0.15 | 5/1/92 | 0.303 | 2/1/95 | 0.301 | 5/1/96 | 0.299 | 1.0 |
| 3.02 | 6" ELL | Outer Radius | 0.15 | 5/1/92 | 0.300 | 2/1/95 | 0.284 | 5/1/96 | 0.276 | 6.0 |
| 3.03 | 6" ELL | Outer Radius | 0.15 | 5/1/92 | 0.307 | 2/1/95 | 0.295 | 5/1/96 | 0.292 | 3.7 |
| 3.04 | 6" ELL | Inner Radius | 0.15 | 5/1/92 | 0.369 | 2/1/95 | 0.366 | 5/1/96 | 0.359 | 2.5 |
| 3.05 | 6" ELL | East | 0.15 | 5/1/92 | 0.326 | 2/1/95 | 0.325 | 5/1/96 | 0.322 | 1.0 |
| 3.06 | 6" ELL | West | 0.15 | 5/1/92 | 0.322 | 2/1/95 | 0.316 | 5/1/96 | 0.311 | 2.7 |
| 4.01 | 6" PIPE | Top | 0.15 | 5/1/92 | 0.320 | 2/1/95 | 0.319 | 5/1/96 | 0.314 | 1.5 |
| 4.02 | 6" PIPE | Bottom | 0.15 | 5/1/92 | 0.313 | 2/1/95 | 0.306 | 5/1/96 | 0.303 | 2.5 |
| 4.03 | 6" PIPE | East | 0.15 | 5/1/92 | 0.328 | 2/1/95 | 0.327 | 5/1/96 | 0.324 | 1.0 |
| 4.04 | 6" PIPE | West | 0.15 | 5/1/92 | 0.321 | 2/1/95 | 0.320 | 5/1/96 | 0.315 | 1.5 |
| 5.01 | 6" ELL | Outer Radius | 0.15 | 5/1/92 | 0.262 | 2/1/95 | 0.258 | 5/1/96 | 0.256 | 1.5 |
| 5.02 | 6" ELL | Outer Radius | 0.15 | 5/1/92 | 0.257 | 2/1/95 | 0.240 | 5/1/96 | 0.222 | 8.7 |
| 5.03 | 6" ELL | Outer Radius | 0.15 | 5/1/92 | 0.268 | 2/1/95 | 0.262 | 5/1/96 | 0.259 | 2.2 |
| 5.04 | 6" ELL | Inner Radius | 0.15 | 5/1/92 | 0.330 | 2/1/95 | 0.326 | 5/1/96 | 0.322 | 2.0 |
| 5.05 | 6" ELL | Top | 0.15 | 5/1/92 | 0.290 | 2/1/95 | 0.282 | 5/1/96 | 0.282 | 2.0 |
| 5.06 | 6" ELL | Bottom | 0.15 | 5/1/92 | 0.281 | 2/1/95 | 0.281 | 5/1/96 | 0.277 | 1.0 |
| 6.01 | 6" ELL | Outer Radius | 0.15 | 5/1/92 | 0.308 | 2/1/95 | 0.261 | 5/1/96 | 0.247 | 15.2 |
| 6.02 | 6" ELL | Outer Radius | 0.15 | 5/1/92 | 0.287 | 2/1/95 | 0.222 | 5/1/96 | 0.182 | 26.2 |
| 6.03 | 6" ELL | Outer Radius | 0.15 | 5/1/92 | 0.285 | 2/1/95 | 0.234 | 5/1/96 | 0.217 | 17.0 |
| 6.04 | 6" ELL | Inner Radius | 0.15 | 5/1/92 | 0.372 | 2/1/95 | 0.371 | 5/1/96 | 0.363 | 2.2 |
| 6.05 | 6" ELL | North | 0.15 | 5/1/92 | 0.325 | 2/1/95 | 0.320 | 5/1/96 | 0.316 | 2.2 |
| 6.06 | 6" ELL | South | 0.15 | 5/1/92 | 0.336 | 2/1/95 | 0.335 | 5/1/96 | 0.333 | 0.8 |
| 7.01 | 6" PIPE | North | 0.15 | 8/1/93 | 0.447 | 2/1/95 | 0.445 | 5/1/96 | 0.442 | 1.8 |
| 7.02 | 6" PIPE | South | 0.15 | 8/1/93 | 0.457 | 2/1/95 | 0.454 | 5/1/96 | 0.451 | 2.2 |
| 7.03 | 6" PIPE | East | 0.15 | 8/1/93 | 0.440 | 2/1/95 | 0.440 | 5/1/96 | 0.437 | 1.1 |
| 7.04 | 4" PIPE | West | 0.15 | 8/1/93 | 0.440 | 2/1/95 | 0.435 | 5/1/96 | 0.432 | 2.9 |
| 8.01 | 4" PIPE | North | 0.15 | 5/1/92 | 0.432 | 2/1/95 | 0.432 | 5/1/96 | 0.422 | 2.5 |
| 8.02 | 4" PIPE | South | 0.15 | 5/1/92 | 0.441 | 2/1/95 | 0.440 | 5/1/96 | 0.437 | 1.0 |
| 8.03 | 4" PIPE | East | 0.15 | 5/1/92 | 0.450 | 2/1/95 | 0.445 | 5/1/96 | 0.443 | 1.7 |
| 8.04 | 4" PIPE | West | 0.15 | 5/1/92 | 0.452 | 2/1/95 | 0.449 | 5/1/96 | 0.445 | 1.7 |

TABLE 1-continued

Inspection And Corrosion Rate Data

| TML | Size & Component Type | Orientation of TML on Component | Minimum Required Thickness | Initial Insp Date | Initial Insp Thickness | Previous Insp Date | Previous Insp Thickness | Last Insp Date | Last Insp Thickness | LTCR mils/yr |
|---|---|---|---|---|---|---|---|---|---|---|
| 9.01 | 4" ELL | Outer Radius | 0.15 | 9/1/92 | 0.422 | 2/1/95 | 0.403 | 5/1/96 | 0.385 | 10.1 |
| 9.02 | 4" ELL | Outer Radius | 0.15 | 9/1/92 | 0.429 | 2/1/95 | 0.405 | 5/1/96 | 0.379 | 13.6 |
| 9.03 | 4" ELL | Outer Radius | 0.15 | 9/1/92 | 0.430 | 2/1/95 | 0.412 | 5/1/96 | 0.397 | 9.0 |
| 9.05 | 4" ELL | North | 0.15 | 9/1/92 | 0.461 | 2/1/95 | 0.459 | 5/1/96 | 0.455 | 1.6 |
| 9.06 | 4" ELL | South | 0.15 | 9/1/92 | 0.435 | 2/1/95 | 0.430 | 5/1/96 | 0.424 | 3.0 |
| 10.01 | 4" PIPE | Top | 0.15 | 5/1/92 | 0.444 | 2/1/95 | 0.442 | 5/1/96 | 0.436 | 2.0 |
| 10.02 | 4" PIPE | Bottom | 0.15 | 5/1/92 | 0.456 | 2/1/95 | 0.455 | 5/1/96 | 0.446 | 2.5 |
| 10.03 | 4" PIPE | North | 0.15 | 5/1/92 | 0.446 | 2/1/95 | 0.435 | 5/1/96 | 0.432 | 3.5 |
| 10.04 | 4" PIPE | South | 0.15 | 5/1/92 | 0.457 | 2/1/95 | 0.452 | 5/1/96 | 0.451 | 1.5 |
| 11.01 | 4" ELL | Outer Radius | 0.15 | 9/1/92 | 0.421 | 2/1/95 | 0.413 | 5/1/96 | 0.404 | 4.6 |
| 11.02 | 4" ELL | Outer Radius | 0.15 | 9/1/92 | 0.418 | 2/1/95 | 0.385 | 5/1/96 | 0.362 | 15.3 |
| 11.03 | 4" ELL | Outer Radius | 0.15 | 9/1/92 | 0.416 | 2/1/95 | 0.405 | 5/1/96 | 0.388 | 7.6 |
| 11.04 | 4" ELL | Inner Radius | 0.15 | 9/1/92 | 0.466 | 2/1/95 | 0.464 | 5/1/96 | 0.460 | 1.6 |
| 11.05 | 4" ELL | North | 0.15 | 5/1/92 | 0.447 | 2/1/95 | 0.446 | 5/1/96 | 0.440 | 1.7 |
| 11.06 | 4" ELL | South | 0.15 | 9/1/92 | 0.459 | 2/1/95 | 0.458 | 5/1/96 | 0.454 | 1.4 |
| 12.01 | 4" ELL | Outer Radius | 0.15 | 9/1/92 | 0.445 | 2/1/95 | 0.440 | 5/1/96 | 0.435 | 2.7 |
| 12.02 | 4" ELL | Outer Radius | 0.15 | 9/1/92 | 0.423 | 2/1/95 | 0.412 | 5/1/96 | 0.394 | 7.9 |
| 12.03 | 4" ELL | Outer Radius | 0.15 | 9/1/92 | 0.432 | 2/1/95 | 0.421 | 5/1/96 | 0.409 | 6.3 |
| 12.04 | 4" ELL | Inner Radius | 0.15 | 9/1/92 | 0.415 | 2/1/95 | 0.415 | 5/1/96 | 0.408 | 1.9 |
| 12.05 | 4" ELL | East | 0.15 | 9/1/92 | 0.441 | 2/1/95 | 0.441 | 5/1/96 | 0.436 | 1.4 |
| 12.06 | 4" ELL | West | 0.15 | 9/1/92 | 0.446 | 2/1/95 | 0.444 | 5/1/96 | 0.440 | 1.6 |

Notes to Table 1:
(1) All thicknesses are in inches
(2) LTCR is expressed in mils of wall thickness loss per year, where 1 mil is 0.001 inch.

Notes to Table 1:

(1) All thicknesses are in inches (2) LTCR is expressed in mils of wall thickness loss per year, where 1 mil is 0.001 inch.

Long term and short term corrosion rates may be calculated in the conventional fashion, in accordance with industry standards (E.g., American Petroleum Institute ("API") 510, 570), such as:

Equation 1:

$$\text{Corrosion Rate} = 1000 \times ((t_1 - t_2)/(d_2 - d_1))$$

Where:

| | Long-Term | Short Term | Units |
|---|---|---|---|
| $t_1$ | initial thickness | previous thickness | inches |
| $t_2$ | last thickness | last thickness | inches |
| $(d_2-d_1)$ | last date - initial date | last date - previous date | years |

Table 1 shows only long term corrosion rates ("LTCR") for purposes of this example. A similar entire analysis may be performed separately for both long term and short term corrosion rates, and the long term vs. short term results compared to determine if any short term corrosion rate acceleration has occurred, which may indicate a more recent process change that will impact reliability of the system. Additionally, other well known methods may be used for determining LTCRs for the 55 TMLs, such as fitting thickness data over time to a linear or other wall loss equation. Next, fifteen corrosion engineering models are generated by organizing the LTCR data according to five corrosion rate physical relationship data groups. As recited above, fewer or more physical relationship data groups could be used depending on complexities of a particular system being analyzed. The five physical relationship data groups selected for this example are shown and further described in Table 2.

TABLE 2

| Physical Relationship Data Group | Meaning of Relationship | System Data Required to Use Relationship |
|---|---|---|
| All TMLs | Single corrosion rate distribution for all TMLs | Two thickness measurements taken on two different dates, per TML |
| TMLs With Different Sizes | Higher or lower fluid velocities, independent of component type produce different corrosion rate distributions | Thickness measurements and component diameters |
| TMLs With Different Components | Similar process conditions within same components produce the same corrosion distribution, but not between components | Thickness measurements and component type identification |
| TMLs With Different Orientations | Local conditions within components produce different corrosion rate distributions | Thickness measurements and orientation of TMLs on components |
| TMLs In Different Zones | Local conditions produce defined zones with different corrosion rate distributions | Thickness measurements and sequential numbering of TMLs through system |

As is apparent, specific physical relationship data groups are based on previous information drawn from the historical corrosion rate data base 22 such as industry standards, inspector experience, failure histories and process conditions. Alternative and new physical relationship data groups may be added as more experience and inspection data is obtained. Such groups may be derived from general relationships applied to all systems, or may be specific to a particular equipment type (e.g., relationships used for piping systems are generally different than those for storage tanks and for vessels such as distillation columns, due to different physical configurations and fluid conditions encountered in these different types of equipment), or the relationships may be process fluid specified. For example, the "TMLs in Different Zones" data group is designed to identify a zone or "pocket" of corrosion within the system (if one exists), caused by locally corrosive conditions such as mixing of two process fluids where the resulting mixture is more corrosive than either of the two process fluids, or such as vapor condensation which forms a corrosive liquid. The particular system defined for this example has no potential for development of such a pocket, however use of the "ZONES" data group 60 may be applied in similar real world situations to confirm that such conditions do not exist. In general no concern arises about using models which may not apply to a particular system, because the groups will either merge into a single distribution, mirroring the "all TMLs" physical relationship data group, or the goodness-of-fit test will not recognize the not-applicable relationship(s) as the best-fitting corrosion engineering model.

The three statistical distributions applied to the system corrosion data 14 coordinated into the aforesaid five physical relationship data groups are:

Equation 2: Normal: $F(r)=\Phi[(r-c)/s]$

Equation 3: Log Normal: $F(r)=\Phi[\{\log(r)-\log(c)\}/\log(s)]$

Equation 4: Weibull: $F(r)=1-\exp(-r/c)^s$

Where:

r is the corrosion rate

F(r) is the fraction occurring at corrosion rate r c is the characteristic rate s is the shape parameter $\Phi$ is the standard normal cumulative distribution function. Note that c and s have different values for each distribution.

These three statistical distributions described in equations 2–4 general provide a satisfactory fit to corrosion rate data, but other known statistical distributions may be used.

The system corrosion data for each physical relationship data group is then fitted to the three statistical distributions using established, well known rank regression or maximum likelihood estimation techniques ("MLE"). Similar distributions within each data group as determined using techniques such as a likelihood ratio test are then merged as shown in FIG. 3, thereby increasing sample size to enhance accuracy of the corrosion engineering model results. An appropriate criteria for a goodness-of-fit test, when using rank regression techniques for fitting the corrosion rate data to the distribution is using the correlation coefficient squared ($r^2$), where the correlation coefficient represents the proportion of the variation that can be explained by the statistical distribution. A correlation coefficient of 1 represents a "perfect" fit to the statistical distribution. Since, in applying the goodness-of-fit tests 50, $r^2$ must be compared between different statistical distributions and between groups having a different number of TMLs, the corrosion engineering model $r^2$ values are compared to a set of critical correlation coefficients squared ($CCC^2$), where the critical correlation coefficients are generated for the particular distribution, the parameters for that particular distribution (parameters c and s from Equations 2–4) and the number of TMLs in the group, are generated using established Monte Carlo techniques. A set of $CCC^2$ values are generated from, for example, 1000 Monte Carlo trials and are then ranked and compared to the actual corrosion engineering model $r^2$ values. The $r^2$ values corresponding to the highest percentile, or "P Value" from the $CCC^2$ represents the best fitting corrosion engineering model. Rank regression techniques are used in this exemplary problem.

Alternatively, if the statistical distributions are fitted using maximum likelihood estimation (MLE) techniques, a value known as the log likelihood well-known in the statistical arts (see Nelson) may be used as a goodness-of-fit test where the corrosion engineering model having the highest log likelihood represents the best fitting model.

For either rank regression or MLE data fitting where sub-populations are identified, there will be more than one goodness-of-fit test result for the corrosion engineering model. The exemplary problem herein demonstrates a case where two P Values are used for several models to determine the goodness-of-fit. In such cases, a simple averaging technique or other methods to pool the P Values or log likelihoods may be used to judge the overall goodness-of-fit.

As shown in Table 3, the corrosion engineering model with the highest "P Values" relating to the correlation coefficients is the "Weibull" distribution, "Orientations" physical relationship data group.

TABLE 3

Running Corrosion Engineering Model Results

| Distribution | Corrosion Rate/ Physical Relationship | Group (Sub-population) | Shape Parameter (s) | Characteristic Rate (c) | $R^2$ | P Value | 99% Reliability Corrosion Rate (mpy) | # TML's In Group |
|---|---|---|---|---|---|---|---|---|
| Log Normal | All | 1 | 2.57 | 2.56 | 0.931 | <1 | 23 | 55 |
| | Components | 1 | 2.73 | 3.35 | 0.947 | 11 | 35 | 35 |
| | | 2 | 1.60 | 1.62 | 0.962 | 49 | 5 | 20 |
| | Orientations | 1 | 1.53 | 1.62 | 0.970 | 39 | 4 | 34 |
| | | 2 | 2.72 | 5.37 | 0.964 | 50 | 55 | 21 |
| | Sizes | 1 | 2.57 | 2.56 | 0.931 | <1 | 23 | 55 |
| | Zones | 1 | 2.57 | 2.56 | 0.931 | <1 | 23 | 55 |
| Normal | All | 1 | 4.93 | 3.87 | 0.668 | <1 | 15 | 55 |
| | Components | 1 | 5.81 | 5.16 | 0.754 | <1 | 19 | 35 |
| | | 2 | 0.84 | 1.78 | 0.987 | 99 | 4 | 20 |
| | Orientations | 1 | 0.75 | 1.78 | 0.989 | 95 | 4 | 34 |
| | | 2 | 6.63 | 8.83 | 0.907 | 10 | 24 | 18 |

TABLE 3-continued

Running Corrosion Engineering Model Results

| Distribution | Corrosion Rate/ Physical Relationship | Group (Sub-population) | Shape Parameter (s) | Characteristic Rate (c) | $R^2$ | P Value | 99% Reliability Corrosion Rate (mpy) | # TML's In Group |
|---|---|---|---|---|---|---|---|---|
| | | 3 | 0.91 | 1.75 | 1.000 | 100 | 4 | 3 |
| | Sizes | 1 | 4.93 | 3.87 | 0.668 | <1 | 15 | 55 |
| | Zones | 1 | 4.93 | 3.87 | 0.668 | <1 | 15 | 55 |
| Weibull | All | 1 | 1.33 | 4.03 | 0.819 | <1 | 13 | 55 |
| | Components | 1 | 1.28 | 5.25 | 0.842 | 1 | 17 | 35 |
| | | 2 | 2.35 | 2.03 | 0.993 | 100 | 4 | 20 |
| | Orientations | 1 | 2.69 | 2.01 | 0.992 | 99 | 4 | 34 |
| | | 2 | 1.13 | 8.39 | 0.985 | 94 | 32 | 21 |
| | Sizes | 1 | 1.33 | 4.03 | 0.819 | <1 | 13 | 55 |
| | Zones | 1 | 1.33 | 4.03 | 0.819 | <1 | 13 | 55 |

Where: The five "physical relationship data groups" of this example are listed in the column labelled as "Corrosion Rate/Physical Relationship"; identified "sub-populations" are listed in a column labelled "Group (Sub-population); and a column entitled "99% Reliability Corrosion Rate (mpy)" represents statistical corrosion rates which have only a 1% chance of being exceeded in each physical relationship data group or sub-population. The 99% reliability level was entered and integrated in FIG. 1, step 26 as the required level of reliability or risk for this system.

Because the Weibull distribution (distr.)/orientations group has the correlation coefficients corresponding to the highest "P Values", this corrosion engineering model best describes the corrosion behavior in this exemplary system and will be used for remaining life predictions and optimum inspection schedules for the system. The Weibull distr./orientation group corrosion engineering model also reveals sub-populations within that data group that are identified in Table 3 as "Group 1" and "Group 2" of the Weibull-Orientations physical relationship data group, and Group 2 has a significantly higher 99% reliability corrosion rate; Group 1 being 4 mpy, and Group 2 being 32 mpy.

It is noted that the Table 3 "99% Reliability Corrosion Rate (mpy)" column figures quantify the system reliability or risk criteria 26 and represent statistical corrosion rates which have only a 1% chance of being exceeded in each physical relationship data group and their sub-populations. In other words, there is a 1% risk, or a probability of 0.01 (1/100) that a higher corrosion rate exists in each data group or sub-population. The probability of a system reaching its retirement thickness by a next inspection date is directly related to the corrosion rate which occurs at a reliability level required for the system. As an added measure of safety, and in accordance with industry standards, the next inspection date is scheduled to occur at a fraction of the remaining life (e.g., the system life until retirement thickness is reached); typically re-inspection occurs at one half of the system remaining life.

In this example as shown in Table 3, the results using the physical relationship data groups identified as "Sizes" and "Zones" produced the same results as the "All TMLs" data group. For the Sizes data group, the TMLs were grouped according to the two different sizes (4" and 6"), but these two resulting size populations were not significantly different from each other, hence the two sub-populations were merged. After merging, only a single population existed which was identical to the "All TMLs" data group. In the case of the "Zones" data group, the best fitting location and length of potential sub-populations were identified for each distribution, but the sub-populations were again found to not be significantly different and were therefore merged into a single population.

Integration of the Table 3 99% reliability corrosion rate or a 1% system risk criteria 26 as shown in FIG. 1 for the Weibull distr./orientations group is as follows:

$$\text{Rate} = c[\ln(1/(1-F(r))]^{1/s} \qquad \text{Equation 5}$$
$$= 2.01[\ln(1/(1-0.99))]^{1/2.69}$$
$$= 3.5 \; mpy$$

This is the 99% reliability corrosion rate for the "Group Sub-population" 1 of Weibull distr./orientations group, which has been rounded to 4 mpy in Table 3.

The remaining life of each TML is then calculated in the conventional manner, in accordance with industry standards by applying the 99% (or other desired) reliability corrosion rate, or probability of retirement factor to the TMLs within a specific group as follows:
Equation 6:

$$\text{Remaining Life} = 1000(t_{act} - t_{min})/r$$

Where:
  $t_{act}$ is the actual minimum thickness in inches
  $t_{min}$ is the minimum required thickness in inches
  r is the data group or sub-population group corrosion rate, evaluated at desired reliability in mils/year Applying the 99% reliability corrosion rates for the respective data groups and sub-population groups to the most recently measured thickness at each TML and calculating the remaining life from Equation 5 above gives the time to reach the retirement thickness, or the "Minimum Required Thickness" shown in Table 1. Those results provide re-inspection dates with a 1.0% likelihood of failure. That is, the remaining life calculation uses the corrosion rate which will result in a 1.0% chance of reaching the retirement age thickness or "minimum required thickness" before the next inspection. As specified above, an optimum inspection schedule would schedule re-inspection at a fraction of the remaining period of time to reach the retirement age. One-half of the remaining period to retirement age is used in this example.

In this example, for TML 3.03, as shown on Table 1 the last thickness is 0.292 inches, and the retirement thickness is 0.150 inches. TML 3.03 is in the Group Sub-population 2 of Weibull distr./orientations group having a 99% corrosion reliability rate of 32 mpy. According to Equation 6, the remaining life is therefore:

Remaining Life$_{TML3.03}$=1000($t_{aci}-t_{min}$)/r=1000(0.292−0.150)/32=4.4 yrs.

If this TML is to be re-inspected at one-half of its remaining life as an optimum inspection schedule, the next inspection would occur at 4.4 yrs/2=2.2 years. Since the last inspection according to Table 1 was May 1, 1996, the next inspection as part of an optimum inspection schedule determined by the method of selective corrosion rate analysis 10 must be no later than Jul. 13, 1998.

The method of selective corrosion rate analysis 10 may also include a step of integration of inspection costs data 36 into the step of generating a remaining life and optimum inspection schedule 20 shown in FIG. 1. For example, if there are a wide range of re-inspection dates due to a presence of multiple corrosion rate distributions or significant variations in component thicknesses, it will not be cost-effective to re-inspect the system as a whole. Alternatively, re-inspecting each TML in its calculated re-inspection date may be employed, however, this may also not be cost-effective due to the time required for access, permits and other preparations for inspecting each TML individually. Once the system corrosion rates at the desired degree of reliability and next inspection dates are determined, an optimum re-inspection schedule may be generated that includes integration of inspection costs data such as permit—preparation time, number of readings taken per unit time (established for both insulated and uninsulated systems with several degrees of access difficulty) and inefficiencies of breaking the system into segments (due to factors such as non-sequential data acquisition), etc. Normally, multiple readings on a given component are always measured together, since these additional measurements can be taken with negligible incremental costs. A total inspection cost for the system is calculated for a fixed period of time, and may even include an inflation factor for the cost. For the exemplary system presented hereinabove, the following assumptions have been used to demonstrate the integration of inspection costs data 36 step of the method of selective corrosion rate analysis 10.

| Inspector's hourly rate | $40.00 |
|---|---|
| TML's inspected per hour | 30 |
| Prep./permit times (hrs) per inspection segment per inspection segment | 0.5 |
| Annual inflation - inspection costs | 5% |
| Maximum no. of inspection segments | 2 |
| Penalty (inspection time multiplier) for additional segment | 1.15 |

A series of re-inspection schedules is then developed, with the re-inspection date for each segment of the system determined by a minimum remaining life within the segment. In this manner, there is no chance of "missing" an inspection date, or in other words, of exceeding a retirement date at the required level of reliability or risk. In addition to calculating the re-inspection costs, a probability of reaching the minimum required retirement thickness at a TML within each inspection segment is also calculated, as shown in the following Table 4.

TABLE 4

Re-Inspection Options - 5 Year Projections

| | Segment 1 | | | Segment 2 | | |
|---|---|---|---|---|---|---|
| Total Cost | # Insp's Req'd | Prob. Of Retirem't | # TML's | # Insp's Req'd | Prob. Of Retirem't | # TML's |
| $3,870 | 10 | 0.00018 | 55 | — | — | — |
| $2,687 | 10 | 0.00018 | 6 | 5 | 0.00018 | 49 |
| $2,346 | 10 | 0.00018 | 12 | 3 | 0.00018 | 43 |
| $2,750 | 10 | 0.00018 | 18 | 3 | 0.00018 | 37 |
| $2,489 | 10 | 0.00018 | 22 | 2 | 0.00018 | 33 |
| $2,730 | 10 | 0.00018 | 28 | 2 | 0.00018 | 27 |
| $2,926 | 10 | 0.00018 | 33 | 2 | 0.00018 | 22 |
| $3,240 | 10 | 0.00018 | 39 | 2 | 0.00018 | 16 |
| $7,110 | 10 | 0.00018 | 43 | 1 | 0.000084 | 12 |
| $6,914 | 10 | 0.00018 | 47 | 1 | 0.000084 | 8 |
| >$10,000 | 10 | 0.00018 | 51 | 1 | 0.000084 | 4 |

A least expensive optimum choice shows a cost of $2,346.00 and requires re-inspecting 12 TMLs a total of 10 times and 43 TMLs three times over a subsequent five year period. Such a frequent re-inspecting of the 12 lowest remaining-life TMLs of Segment 1 is much more intensive than the two re-inspections of the 43 TMLs of Segment 2, however that optimum inspection schedule is still much less costly than re-inspecting all 55 TMLs at each of the 10 inspections over the five year period. This optimum inspection schedule shows a much lower probability of retirement, based on all of the possible inspection schedules listed in Table 4, than the system allowable probability of retirement at any TML of 0.01. It is noted that a probability of retirement in Table 4 considers that the TMLs will be inspected at one-half of their remaining life and assumes that the system corrosivity does not change from corrosion rate distributions defined by data used in the analysis. However, an actual probability of retirement in a real world situation will be no greater than 1% and no less than values shown in Table 4 for a selected inspection schedule.

The probability that a TML in the system will reach a retirement thickness by the next inspection date (or other desired date) may be found using a 99% reliability (or other selected reliability level) corrosion rate for the specific group, the distribution parameters (Table 3) for the group and equation 4. The following illustrates calculation of the probability that retirement will occur at a TML by the re-inspection date, using half-life re-inspection criteria and not maximum reinspection interval, to simplify the calculations. A group 2 TML ("Group 2 TML) from the exemplary system is used.

The maximum tolerable corrosion rate (the rate which, if exceeded, will result in retirement prior to the next inspection) for a TML is twice the 99% reliability rate when a half-life re-inspection criteria is used (given that retirement occurs at the end of remaining life, based on the 99% reliability rate) or 2×32=64 mils/yr for the Group 2 TML. Using a rearrangement of Equation 4 with parameters c and s from Table 3 (8.39 and 1.13 respectively), the probability of experiencing 64 mils/year in Group 2 TML is:

$1-F(r)=\exp(64/8.39)^{1.13}=0.00018$

This is the desired probability of retirement, corresponding to a worst-case probability of retirement in Table 4.

Based on results of the above example, conclusions from running the corrosion engineering models 16 may be drawn to identify additional trends. Characteristics of the physical relationship data groups and identified sub-populations show a clear pattern which provides valuable information regarding actual corrosion mechanisms at work in the system. In particular and as a further example, within the corrosion engineering model that demonstrated the best goodness-of-fit test results, namely the Weibull distr.-Orientations, and its sub-populations listed in Table 3 as Group 1 and Group 2, the distinguishing characteristic of the Group 1 TMLs is that the TMLs were grouped according to their positions at orientations except "Outer Radius". The distinguishing characteristic of the Group 2 TMLs is that they were grouped according to their positions at "Outer Radius" orientations. Group 1 had a 99% Reliability Corrosion Rate in mils per year of 4, while Group 2 had a Rate of 32, as indicated by Table 3.

Consequently, it can be seen that there are erosive materials at high velocity present in the process stream, because the corrosion rate is significantly higher at changes in direction mechanical components in the system, such as at an outer radius of an elbow. An increase in velocity mandated by smaller diameter mechanical components has no significant impact on the corrosion rate. Additionally, analysis of the results of running of the corrosion engineering models likewise reveals that there are no uncovered zones of high corrosion rates to suggest a presence of unfavorable fluid mixtures or fluid phase changes. Further, there is no evidence of deposits in low areas, nor stratification of different fluids often seen in low velocity systems.

Consequently, this example of application of the method of selective corrosion rate analysis has been able to suggest an active corrosion mechanism, enabling an inspector and/or engineer to take appropriate steps to reduce the corrosion rate and increase the remaining life of the mechanical components of the system. Analysis of data results from application of the method of selective corrosion rate analysis reveals important trends and provides information about actual corrosion mechanisms because the method makes maximum use of the historical system corrosion data as well as data generated with each inspection and run through a corrosion engineering model that best describes the actual system corrosion behavior. Additionally, a statistical analysis of results of application of the method of selective corrosion rate analysis may assist in identifying corrosion trends. For example, the distribution of corrosion rates may be examined over time to identify signs of acceleration in the corrosion rate. Specifically, when three sets of TML thicknesses are available, the long term and short term corrosion rates may be compared using the log likelihood ratio test described above (for determining if two physical relationship data groups are not significantly different) and any significant differences can be reported. A similar exercise can be performed if a change in materials of construction or if process/feedstock changes were made and it is of interest to know if the system was impacted by these changes. Examination of the individual distribution parameters (s and c in Equations 2–4) and trends in these parameters can reveal important system reliability information. The s (shape) parameter is a measure of a range of corrosion rates in a system where a wide range indicates non-uniform corrosion. Shape parameter (s) ratios are excellent measures of non-uniform corrosion trends.

The c (characteristic rate) parameter is a measure of the central tendency of the system corrosion rates. Thus, by examining the trends in these parameters, it is possible to determine if the corrosion mechanism is tending toward more or less uniform rates and/or if the mean rate is increasing or decreasing. The s and c parameters can also be compared for all systems within a unit, or between process units to quantify the degree of non-uniform corrosion and to rank a central tendency rate. Generally, systems with non-uniform corrosion and higher characteristic rates are candidates for further study or confirmation inspections using alternate inspection techniques such as radiography. Knowledge that a particular system in a process unit or plant including multiple systems falls into a worst 5% in the process unit for non-uniform corrosion or a highest 5% mean rate in the entire plant is an important reliability trend and would be available from statistics within the corrosion engineering model library.

Armed with such information, an inspector or engineer can focus on the process and/or equipment changes which may produce such trends. The method of selective corrosion rate analysis may even be added to more conventional remaining life estimation for a primary purpose of trend analysis to assist in identifying actual corrosion mechanisms at work in a particular system.

While the method of selective corrosion rate analysis has been described and illustrated with respect to a particular application, it will be understood by those skilled in the art that the present invention is not limited to this particular example. Accordingly, reference should be made primarily to the following claims rather than to the foregoing specification to determine the scope of the invention.

What is claimed is:

1. A method of selective corrosion rate analysis for generating an inspection schedule for a fluid processing plant, comprising the steps of:
   a. identifying a system from a division of the plant into one or more systems wherein each system has mechanical fluid containment components that are expected to experience a common corrosive environment and each system has at least one thickness measurement location for performing thickness inspections;
   b. establishing system corrosion data for each thickness measurement location in the system;
   c. running the system corrosion data through a plurality of corrosion engineering models; and
   d. selecting a best fitting corrosion engineering model for generating a remaining life and optimum inspection schedule for each thickness measurement location in the system by running the system corrosion data through the selected best fitting corrosion engineering model.

2. The method of selective corrosion rate analysis of claim 1, wherein the step of running the system corrosion data through a plurality of corrosion engineering models comprises the further steps of coordinating the system corrosion data for each thickness measurement location into a plurality of physical relationship data groups, applying a plurality of statistical distributions to each physical relationship data group, and applying a goodness-of-fit test to results of application of the statistical distributions to identify a combination of a physical relationship data group and statistical distribution as the best fitting corrosion engineering model that most accurately describes actual system corrosion behavior.

3. The method of selective corrosion rate analysis of claim 2, wherein the step of running the system corrosion data through a plurality of corrosion engineering models comprises the further step of combining results of the statistical distributions that are not significantly different and identifying as sub-populations results of the statistical distributions that vary significantly from statistical distribution results of other physical relationship data groups and applying the goodness-of-fit test to the sub-population results.

4. The method of selective corrosion rate analysis of claim 2, wherein the step of coordinating the system corrosion data for each thickness measurement location into a plurality of physical relationship data groups further comprises a step of coordinating the system corrosion data for each thickness measurement location into at least a first group having all of the system thickness measurement locations grouped randomly and a second group having all the thickness measurement locations grouped according to different sized mechanical components in which the thickness measurement locations are located.

5. The method of selective corrosion rate analysis of claim 4, wherein the step of coordinating the system corrosion data for each thickness measurement location into a plurality of physical relationship data groups further comprises a step of coordinating the system corrosion data for each thickness measurement location into at least a third group having all the system thickness measurement locations grouped according to different mechanical components in which the thickness measurement locations are located.

6. The method of selective corrosion rate analysis of claim 5, wherein the step of coordinating the system corrosion data for each thickness measurement location into a plurality of physical relationship data groups further comprises a step of coordinating the system corrosion data for each thickness measurement location into at least a fourth group having all the system thickness measurement locations grouped according to their differing orientations within mechanical components.

7. The method of selective corrosion rate analysis of claim 6, wherein the step of coordinating the system corrosion data for each thickness measurement location into a plurality of physical relationship data groups further comprises a step of coordinating the system corrosion data for each thickness measurement location into at least a fifth group having some system thickness measurement locations grouped according to a consecutive positional location of the thickness measurement locations defining a zone of higher corrosion rates than other thickness measurement locations grouped according to their locations being outside the zone.

8. The method of selective corrosion rate analysis of claim 1, further comprising transferring operational information to a corrosion engineering model library, the operational information being drawn from selection of the best fitting model and from a statistical analysis applied to all thickness measurement locations after generating the remaining life and optimum inspection schedule, wherein the corrosion engineering model library integrates the operational information and passes the information to an historical corrosion rate data base to modify system corrosion data for each thickness measurement location and thereby effect subsequent running of the corrosion engineering models.

9. The method of selective corrosion rate analysis of claim 1, further comprising a step of integrating system risk reliability criteria after the selecting a best fitting corrosion engineering model step and before the generating an optimum inspection schedule step, wherein the system risk reliability criteria defines a risk-reliability level for the system based on system risk considerations.

10. The method of selective corrosion rate analysis of claim 1, further comprising a step of integrating inspection costs data into the step of generating an optimum inspection schedule step.

11. A method of selective corrosion rate analysis for generating an inspection schedule for a fluid processing plant, comprising the steps of:

a. identifying a system from a division of the plant into one or more systems wherein each system has mechanical fluid containment components that are expected to experience a common corrosive environment and each system has at least one thickness measurement location for performing thickness inspections;

b. establishing for each thickness measurement location system corrosion data drawn from an historical corrosion rate data base;

c. running the system corrosion data through a plurality of corrosion engineering models, including coordinating the system corrosion data for each thickness measurement location into a plurality of physical relationship data groups the data groups being at least a first group having all of the thickness measurement locations grouped randomly and a second group having all system thickness measurement locations grouped according to different sized mechanical components in which the thickness measurement locations are located, applying a plurality of statistical distributions to each physical relationship data group, and applying a goodness-of-fit test to results of application of the statistical distributions to identify a combination of a physical relationship data group and statistical distribution as a best fitting corrosion engineering model that most accurately describes actual system corrosion behavior;

d. selecting the best fitting corrosion engineering model for generating a remaining life and optimum inspection schedule for each thickness measurement location in the system by running the system corrosion data through the selected best fitting corrosion engineering model; and repeating steps a,b,c,d for each system in the plant.

12. The method of selective corrosion rate analysis of claim 11, further comprising a step of integrating system risk reliability criteria after the selecting a best fitting corrosion engineering model step and before the generating an optimum inspection schedule step, wherein the system risk reliability criteria defines a risk-reliability level for the system based on system risk considerations.

13. The method of selective corrosion rate analysis of claim 12, further comprising a step of integrating inspection costs data into the step of generating an optimum inspection schedule step.

14. The method of selective corrosion rate analysis of claim 13, further comprising transferring operational information to a corrosion engineering model library, the operational information being drawn from selection of the best fitting model and from a statistical analysis applied to all thickness measurement locations after generating the remaining life and optimum inspection schedule, wherein the corrosion engineering model library integrates the operational information and passes the information to an historical corrosion rate data base to modify system corrosion data for each thickness measurement location and thereby effect subsequent running of the corrosion engineering models.

15. The method of selective corrosion rate analysis of claim 14, wherein the step of running the system corrosion data through a plurality of corrosion engineering models comprises the further step of combining results of the statistical distributions that are not significantly different and identifying as sub-populations results of the statistical distributions that vary significantly from statistical distribution results of other physical relationship data groups and applying the goodness-of-fit test to the sub-population results.

16. The method of selective corrosion rate analysis of claim 15, wherein the step of coordinating the system corrosion data for each thickness measurement location into a plurality of physical relationship data groups further comprises a step of coordinating the system corrosion data for each thickness measurement location into at least a third group having all system thickness measurement locations grouped according to different mechanical components in which the locations are located, a fourth group having all system thickness measurement locations grouped according to their differing orientations within the mechanical components, and a fifth group having some system thickness measurement locations grouped according to a consecutive positional location of the locations defining a zone of higher corrosion rates than other thickness measurement locations grouped according to their locations being outside the zone.

17. A method of selective corrosion rate analysis for generating an inspection schedule for a fluid processing plant, comprising the steps of:

a. identifying a system from a division of the plant into one or more systems wherein each system has mechanical fluid containment components that are expected to experience a common corrosive environment and each system has at least one thickness measurement location for performing thickness inspections;

b. establishing system corrosion data for each thickness measurement location in the system;

c. running the system corrosion data through a plurality of corrosion engineering models including applying a plurality of statistical distributions to a plurality of physical relationship data groups, wherein the plurality of statistical distributions include at least a Normal, a Log Normal and a Weibull statistical distribution; and d. selecting a best fitting corrosion engineering model for generating a remaining life and optimum inspection schedule for each thickness measurement location in the system by running the system corrosion data through the selected best fitting corrosion engineering model.

18. The method of selective corrosion rate analysis of claim 17, wherein the step of running the system corrosion data through a plurality of corrosion engineering models comprises the further steps of coordinating the system corrosion data for each thickness measurement location into a plurality of physical relationship data groups, applying the plurality of statistical distributions to each physical relationship data group, and applying a goodness-of-fit test to results of application of the statistical distributions to identify a combination of a physical relationship data group and statistical distribution as the best fitting corrosion engineering model that most accurately describes actual system corrosion behavior.

19. The method of selective corrosion rate analysis of claim 18, further comprising a step of integrating inspection costs data into the step of generating an optimum inspection schedule step.

20. The method of selective corrosion rate analysis of claim 19, further comprising a step of integrating system risk reliability criteria after the selecting a best fitting corrosion engineering model step and before the generating an optimum inspection schedule step, wherein the system risk reliability criteria defines a risk-reliability level for the system based on system risk considerations.

* * * * *